(12) United States Patent
Klomhaus (10) Patent No.: US 8,634,891 B2
(45) Date of Patent: Jan. 21, 2014

(54) METHOD AND SYSTEM FOR SELF REGULATION OF SENSOR COMPONENT CONTACT PRESSURE

(75) Inventor: Jill Klomhaus, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1148 days.

(21) Appl. No.: 12/469,476

(22) Filed: May 20, 2009

(65) Prior Publication Data

US 2010/0298678 A1    Nov. 25, 2010

(51) Int. Cl.
*A61B 5/00*    (2006.01)

(52) U.S. Cl.
USPC .......................................... 600/344

(58) Field of Classification Search
USPC ................................. 600/310, 344
See application file for complete search history.

(56) References Cited

U.S. PATENT DOCUMENTS

| | | | |
|---|---|---|---|
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

3M Application Guidelines, 3M Acrylic Foam Tape and 3M Acrylic Plus Tape, Oct. 2005, pp. 1-43.*

(Continued)

*Primary Examiner* — Brian Szmal
(74) *Attorney, Agent, or Firm* — Fletcher Yoder (57) ABSTRACT

A method and system for regulating contact pressure of a sensor is provided. In accordance with an embodiment, a sensor includes a collapsible material capable of regulating the localized component contact pressure exerted on a tissue between a threshold which ensures proper contact between the sensing component and monitoring site but which minimizes incidents of excessive localized pressures which could result in tissue damage over prolonged use. This localized contact pressure range is maintained over a wide range of sensor application pressures. In one embodiment, a window is provided in the sensor and a colorimetric indication of the compression or expansion of the collapsible material may be determined through the window.

16 Claims, 5 Drawing Sheets

(56) References Cited

U.S. PATENT DOCUMENTS

| | | |
|---|---|---|
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |

(56) References Cited

U.S. PATENT DOCUMENTS

| | | | |
|---|---|---|---|
| 5,431,170 | A | 7/1995 | Mathews |
| 5,437,275 | A | 8/1995 | Amundsen et al. |
| 5,438,986 | A | 8/1995 | Disch et al. |
| 5,448,991 | A | 9/1995 | Polson et al. |
| 5,452,717 | A | 9/1995 | Branigan et al. |
| 5,465,714 | A | 11/1995 | Scheuing |
| 5,469,845 | A | 11/1995 | DeLonzor et al. |
| RE35,122 | E | 12/1995 | Corenman et al. |
| 5,474,065 | A | 12/1995 | Meathrel et al. |
| 5,482,034 | A | 1/1996 | Lewis et al. |
| 5,482,036 | A | 1/1996 | Diab et al. |
| 5,483,646 | A | 1/1996 | Uchikoga |
| 5,485,847 | A | 1/1996 | Baker, Jr. |
| 5,490,505 | A | 2/1996 | Diab et al. |
| 5,490,523 | A | 2/1996 | Isaacson et al. |
| 5,491,299 | A | 2/1996 | Naylor et al. |
| 5,494,032 | A | 2/1996 | Robinson et al. |
| 5,497,771 | A | 3/1996 | Rosenheimer |
| 5,499,627 | A | 3/1996 | Steuer et al. |
| 5,503,148 | A | 4/1996 | Pologe et al. |
| 5,505,199 | A | 4/1996 | Kim |
| 5,507,286 | A | 4/1996 | Solenberger |
| 5,511,546 | A | 4/1996 | Hon |
| 5,517,988 | A | 5/1996 | Gerhard |
| 5,520,177 | A | 5/1996 | Ogawa et al. |
| 5,521,851 | A | 5/1996 | Wei et al. |
| 5,522,388 | A | 6/1996 | Ishikawa et al. |
| 5,524,617 | A | 6/1996 | Mannheimer |
| 5,529,064 | A | 6/1996 | Rall et al. |
| 5,533,507 | A | 7/1996 | Potratz et al. |
| 5,551,423 | A | 9/1996 | Sugiura |
| 5,551,424 | A | 9/1996 | Morrison et al. |
| 5,553,614 | A | 9/1996 | Chance |
| 5,553,615 | A | 9/1996 | Carim et al. |
| 5,555,882 | A | 9/1996 | Richardson et al. |
| 5,558,096 | A | 9/1996 | Palatnik |
| 5,560,355 | A | 10/1996 | Merchant et al. |
| 5,564,417 | A | 10/1996 | Chance |
| 5,575,284 | A | 11/1996 | Athan et al. |
| 5,575,285 | A | 11/1996 | Takanashi et al. |
| 5,577,500 | A | 11/1996 | Potratz |
| 5,582,169 | A | 12/1996 | Oda et al. |
| 5,584,296 | A | 12/1996 | Cui et al. |
| 5,588,425 | A | 12/1996 | Sackner et al. |
| 5,588,427 | A | 12/1996 | Tien |
| 5,590,652 | A | 1/1997 | Inai |
| 5,595,176 | A | 1/1997 | Yamaura |
| 5,596,986 | A | 1/1997 | Goldfarb |
| 5,611,337 | A | 3/1997 | Bukta |
| 5,617,852 | A | 4/1997 | MacGregor |
| 5,619,992 | A | 4/1997 | Guthrie et al. |
| 5,626,140 | A | 5/1997 | Feldman et al. |
| 5,630,413 | A | 5/1997 | Thomas et al. |
| 5,632,272 | A | 5/1997 | Diab et al. |
| 5,632,273 | A | 5/1997 | Suzuki |
| 5,634,459 | A | 6/1997 | Gardosi |
| 5,638,593 | A | 6/1997 | Gerhardt et al. |
| 5,638,818 | A | 6/1997 | Diab et al. |
| 5,645,060 | A | 7/1997 | Yorkey et al. |
| 5,645,440 | A | 7/1997 | Tobler et al. |
| 5,660,567 | A | 8/1997 | Nierlich et al. |
| 5,662,105 | A | 9/1997 | Tien |
| 5,662,106 | A | 9/1997 | Swedlow et al. |
| 5,666,952 | A | 9/1997 | Fuse et al. |
| 5,671,529 | A | 9/1997 | Nelson |
| 5,673,692 | A | 10/1997 | Schulze et al. |
| 5,673,693 | A | 10/1997 | Solenberger |
| 5,676,139 | A | 10/1997 | Goldberger et al. |
| 5,676,141 | A | 10/1997 | Hollub |
| 5,678,544 | A | 10/1997 | DeLonzor et al. |
| 5,680,857 | A | 10/1997 | Pelikan et al. |
| 5,685,299 | A | 11/1997 | Diab et al. |
| 5,685,301 | A | 11/1997 | Klomhaus |
| 5,687,719 | A | 11/1997 | Sato et al. |
| 5,687,722 | A | 11/1997 | Tien et al. |
| 5,692,503 | A | 12/1997 | Kuenstner |
| 5,692,505 | A | 12/1997 | Fouts |
| 5,709,205 | A | 1/1998 | Bukta |
| 5,713,355 | A | 2/1998 | Richardson et al. |
| 5,724,967 | A | 3/1998 | Venkatachalam |
| 5,727,547 | A | 3/1998 | Levinson et al. |
| 5,731,582 | A | 3/1998 | West |
| D393,830 | S | 4/1998 | Tobler et al. |
| 5,743,260 | A | 4/1998 | Chung et al. |
| 5,743,263 | A | 4/1998 | Baker, Jr. |
| 5,746,206 | A | 5/1998 | Mannheimer |
| 5,746,697 | A | 5/1998 | Swedlow et al. |
| 5,752,914 | A | 5/1998 | DeLonzor et al. |
| 5,755,226 | A | 5/1998 | Carim et al. |
| 5,758,644 | A | 6/1998 | Diab et al. |
| 5,760,910 | A | 6/1998 | Lepper, Jr. et al. |
| 5,766,125 | A | 6/1998 | Aoyagi et al. |
| 5,766,127 | A | 6/1998 | Pologe et al. |
| 5,769,785 | A | 6/1998 | Diab et al. |
| 5,772,587 | A | 6/1998 | Gratton et al. |
| 5,774,213 | A | 6/1998 | Trebino et al. |
| 5,776,058 | A | 7/1998 | Levinson et al. |
| 5,776,059 | A | 7/1998 | Kaestle |
| 5,779,630 | A | 7/1998 | Fein et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,782,758 | A | 7/1998 | Ausec et al. |
| 5,786,592 | A | 7/1998 | Hök |
| 5,790,729 | A | 8/1998 | Pologe et al. |
| 5,792,052 | A | 8/1998 | Isaacson et al. |
| 5,795,292 | A | 8/1998 | Lewis et al. |
| 5,797,841 | A | 8/1998 | DeLonzor et al. |
| 5,800,348 | A | 9/1998 | Kaestle |
| 5,800,349 | A | 9/1998 | Isaacson et al. |
| 5,803,910 | A | 9/1998 | Potratz |
| 5,807,246 | A | 9/1998 | Sakaguchi et al. |
| 5,807,247 | A | 9/1998 | Merchant et al. |
| 5,807,248 | A | 9/1998 | Mills |
| 5,810,723 | A | 9/1998 | Aldrich |
| 5,810,724 | A | 9/1998 | Gronvall |
| 5,813,980 | A | 9/1998 | Levinson et al. |
| 5,817,008 | A | 10/1998 | Rafert et al. |
| 5,817,009 | A | 10/1998 | Rosenheimer et al. |
| 5,817,010 | A | 10/1998 | Hibl |
| 5,818,985 | A | 10/1998 | Merchant et al. |
| 5,820,550 | A | 10/1998 | Polson et al. |
| 5,823,950 | A | 10/1998 | Diab et al. |
| 5,823,952 | A | 10/1998 | Levinson et al. |
| 5,827,182 | A | 10/1998 | Raley et al. |
| 5,830,135 | A | 11/1998 | Bosque et al. |
| 5,830,136 | A | 11/1998 | DeLonzor et al. |
| 5,830,137 | A | 11/1998 | Scharf |
| 5,839,439 | A | 11/1998 | Nierlich et al. |
| RE36,000 | E | 12/1998 | Swedlow et al. |
| 5,842,979 | A | 12/1998 | Jarman et al. |
| 5,842,981 | A | 12/1998 | Larsen et al. |
| 5,842,982 | A | 12/1998 | Mannheimer |
| 5,846,190 | A | 12/1998 | Woehrle |
| 5,851,178 | A | 12/1998 | Aronow |
| 5,851,179 | A | 12/1998 | Ritson et al. |
| 5,853,364 | A | 12/1998 | Baker, Jr. et al. |
| 5,860,919 | A | 1/1999 | Kiani-Azarbayjany et al. |
| 5,865,736 | A | 2/1999 | Baker, Jr. et al. |
| 5,871,442 | A | 2/1999 | Madarasz et al. |
| 5,879,294 | A | 3/1999 | Anderson et al. |
| 5,885,213 | A | 3/1999 | Richardson et al. |
| 5,890,929 | A | 4/1999 | Mills et al. |
| 5,891,021 | A | 4/1999 | Dillon et al. |
| 5,891,022 | A | 4/1999 | Pologe |
| 5,891,024 | A | 4/1999 | Jarman et al. |
| 5,891,025 | A | 4/1999 | Buschmann et al. |
| 5,891,026 | A | 4/1999 | Wang et al. |
| 5,902,235 | A | 5/1999 | Lewis et al. |
| 5,910,108 | A | 6/1999 | Solenberger |
| 5,911,690 | A | 6/1999 | Rall |
| 5,912,656 | A | 6/1999 | Tham et al. |
| 5,913,819 | A | 6/1999 | Taylor et al. |

(56) References Cited

U.S. PATENT DOCUMENTS

| | | |
|---|---|---|
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |

(56) References Cited

U.S. PATENT DOCUMENTS

| | | |
|---|---|---|
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |

(56) References Cited

U.S. PATENT DOCUMENTS

| | | |
|---|---|---|
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,341,559 B2 | 3/2008 | Schultz et al. |
| RE41,317 E * | 5/2010 | Parker .......................... 600/344 |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |

(56) References Cited

U.S. PATENT DOCUMENTS

| | | |
|---|---|---|
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0020179 A1 | 1/2006 | Anderson et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0264727 A1 | 11/2006 | Mannheimer et al. |
| 2006/0276700 A1 | 12/2006 | O'Neil |
| 2007/0027376 A1 | 2/2007 | Todokoro et al. |
| 2007/0032710 A1 | 2/2007 | Raridan et al. |
| 2007/0032712 A1 | 2/2007 | Raridan et al. |
| 2007/0032713 A1 | 2/2007 | Eghbal et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0078316 A1 | 4/2007 | Hoarau |
| 2007/0197887 A1 | 8/2007 | Lunak et al. |
| 2007/0260131 A1 | 11/2007 | Chin |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076996 A1 | 3/2008 | Hoarau |
| 2008/0208023 A1 | 8/2008 | Gruvac et al. |

FOREIGN PATENT DOCUMENTS

| | | |
|---|---|---|
| DE | 19632361 | 2/1997 |
| DE | 19640807 | 9/1997 |
| EP | 0127947 | 12/1984 |
| EP | 0204259 | 12/1986 |
| EP | 0531631 | 3/1993 |
| EP | 0630203 | 12/1994 |
| EP | 0724860 | 8/1996 |
| FR | 2685865 | 7/1993 |
| JP | 2111343 | 4/1990 |
| JP | 3245042 | 10/1991 |
| JP | 3116259 | 12/1991 |
| JP | 3116260 | 12/1991 |
| JP | 4191642 | 7/1992 |
| JP | 5049625 | 3/1993 |
| JP | 6014906 | 1/1994 |
| JP | 6154177 | 6/1994 |
| JP | 6269430 | 9/1994 |
| JP | 7001273 | 1/1995 |
| JP | 7236625 | 9/1995 |
| JP | 10216115 | 8/1998 |
| JP | 10337282 | 12/1998 |
| JP | 2000237170 | 9/2000 |
| JP | 2002224088 | 8/2002 |
| JP | 2003210438 | 7/2003 |
| JP | 2003275192 | 9/2003 |
| JP | 2004089546 | 3/2004 |
| JP | 2004159810 | 6/2004 |
| JP | 2004248820 | 9/2004 |
| JP | 2004329406 | 11/2004 |
| JP | 2004329607 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9111137 | 8/1991 |
| WO | WO9221281 | 12/1992 |
| WO | WO9403102 | 2/1994 |
| WO | WO9502358 | 1/1995 |
| WO | WO9512349 | 5/1995 |
| WO | WO9736536 | 10/1997 |
| WO | WO9749330 | 12/1997 |
| WO | WO9857577 | 12/1998 |
| WO | WO9947039 | 9/1999 |
| WO | WO0059374 | 10/2000 |
| WO | 0167946 A1 | 9/2001 |
| WO | WO02062213 | 8/2002 |
| WO | WO03039326 | 5/2003 |
| WO | WO2005009221 | 2/2005 |
| WO | WO2005010567 | 2/2005 |
| WO | WO2005010568 | 2/2005 |
| WO | 2008/038223 A2 | 4/2008 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measure-*

(56) References Cited

OTHER PUBLICATIONS ment Technology Conference, Ottawa, Canada; May 19-21, 1997; pp. 102-104.

DeKock, Marc; "Pulse Oximetry Probe Adhesive Disks: a Potential for Infant Aspiration," Anesthesiology, vol. 89, pp. 1603-1604 (1998).

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Such, Hans Olaf; "Optoelectronic Non-invasive Vascular Diagnostics Using multiple Wavelength and Imaging Approach," Dissertation, (1998).

Ferrell, T.L., et al.; "Medical Telesensors," SPIE, vol. 3253, pp. 193-198 (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the $22^{nd}$ Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the $22^{nd}$ Annual EMBS International Conference, Chicago, Illinois; Jul. 23-28, 2000; pp. 2796.

Schulz, Christian Eric; "Design of a Pulse Oximetry Sensor Housing Assembly," California State University Master's Thesis, UMI Dissertation Services, UMI No. 1401306, (May 2000) 63 pages.

Aoyagi, T., et al.; "Pulse Oximeters: background, present and future," Neonatal Care, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," Sensor and Actuators, vol. B-76, pp. 527-530 (2001).

Cysewska-Sobusaik, Anna; "Metrological Problems With noninvasive Transillumination of Living Tissues," Proceedings of SPIE, vol. 4515, pp. 15-24 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Lopez-Silva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Tobata, H., et al.; "Study of Ambient Light Affecting Pulse Oximeter Probes," Ikigaku (Medical Technology), vol. 71, No. 10, pp. 475-476 (2002) (Article in Japanese—contains English summary of article).

Irie, A., et al.; "Respiration Monitors—Pulse Oximeters," Neonatal Care, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Cyrill, D., et al.; "Adaptive Comb Filter for Quasi-Periodic Physiologic Signals," Proceedings of the $25^{th}$ Annual International Conference of the IEEE EMBS, Cancun, Mexico, Sep. 17-21, 2003; pp. 2439-2442.

Aoyagi, Takuo; "Pulse oximetry: its invention, theory, and future," Journal of Anesthesia, vol. 17, pp. 259-266 (2003).

Itoh, K., et al.; "Pulse Oximeter," Toyaku Zasshi (Toyaku Journal), vol. 25, No. 8, pp. 50-54 (2003) (Article in Japanese—contains English summary of article).

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Johnston, William S., et al.; "Effects of Motion Artifacts on helmet-Mounted Pulse Oximeter Sensors," 2 pgs. (2004).

Matsuzawa, Y., et al.; "Pulse Oximeter," Home Care Medicine, pp. 42-45 (Jul. 2004); (Article in Japanese—contains English summary of article).

Urquhart, C., et al.; "Ear probe pulse oximeters and neonates," Anaesthesia, vol. 60, p. 294 (2005).

Bentley, David J. et al.; "Measure Pressure with Thin Film"; Paper Film & Foil Converter; May 1, 2003.

International Search Report PCT/US2010/034226, 5 pages, mailed Oct. 21, 2010.

* cited by examiner

METHOD AND SYSTEM FOR SELF REGULATION OF SENSOR COMPONENT CONTACT PRESSURE

BACKGROUND

The present disclosure relates generally to medical sensors and, more particularly, to a sensor which self-adjusts and optimizes contact pressure at a sensing site to accommodate for variations in applied pressures resulting in reduced incidents of tissue damage while improving sensor signal quality.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a fixture of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood characteristics of a patient. For example, a pulse oximeter may be utilized to monitor the blood oxygen saturation of hemoglobin in arterial blood, the relative change in volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light into a patient's tissue and that photoelectrically detects the transmitted and/or scattered light in such tissue. A photo-plethysmographic waveform, which corresponds to the cyclic attenuation of optical energy through the patient's tissue, may be generated from the detected light. Additionally, one or more of the above physiological characteristics may be calculated based generally upon the amount of light transmitted or scattered. More specifically, the light passed through the tissue may be selected to be of one or more wavelengths that may be absorbed or scattered by the blood in an amount correlative to the amount of the blood constituent present in the blood. The amount of light transmitted and/or scattered may then be used to estimate the amount of blood constituent in the tissue using various algorithms.

Inaccuracies in physiological measurements may occur due to improper application of a sensor to a patient. For example, if a sensor is wrapped too tightly around a patient's digit, pressure from the sensor may exsanguinate the tissue at the sensor site such that blood flow through the tissue is reduced. If blood is not allowed to flow normally through the sensor site due to the pressure applied by the sensor, readings from the sensor may be compromised. In addition, excessive localized pressure points between the sensing components and the patient's tissue over an extended time duration can result in pressure sores.

Further, if the sensor is applied loosely to the tissue, other types of inaccuracy may result. For example, if the sensor is too loose, i.e., the sensing components are not held with sufficient pressure against the tissue to ensure proper contact, light shunting may occur where the light transmitted by the emitting component reaches the detector component without passing through the patient's tissue. In some circumstances where the sensor is loose, excessive ambient light from the environment, i.e., light not emitted by the light emitting components of the sensor, may also reach the detector on the sensor, thereby compromising sensor performance. Thus, proper contact between the sensing components and the patient's tissue may be desirable.

In the course of patient monitoring, careful attention by the clinician to apply the sensor with the appropriate applied pressure to ensure proper contact between the sensing components and the patient's tissue, without resulting in excessive localized pressure, can be time consuming. This invention allows the sensor to operate appropriately under a wider range of sensor application pressures by improving the sensor performance while reducing the incidents of excessive localized pressures.

BRIEF DESCRIPTION OF THE DRAWINGS

Advantages of the invention may become apparent upon reading the following detailed description and upon reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It may be useful for a sensor, such as may be used for pulse oximetry or other spectrophotometric applications, to provide a mechanism which self compensates for variations in sensor application pressure by ensuring that the appropriate pressure, localized at the sensing components, provides the necessary intimate contact between the components and the sensing site for optimal performance while minimizing excessive localized pressure which could cause tissue damage if prolonged. For example, in an embodiment described herein, a collapsible material may be used to form a layer or pocket of the sensor such that the amount of pressure applied by the sensing components is within a desired range. In an embodiment, it may be desirable to provide a sensor that given variations in application pressure can regulate the localized pressure at the sensing component site to provide a pressure high enough to ensure intimate contact between the sensing components and the sensing site but low enough to minimize tissue damage or discomfort. With this in mind, a monitoring system suitable for use with a sensor constructed in accordance with such considerations is provided.

Figure 1:
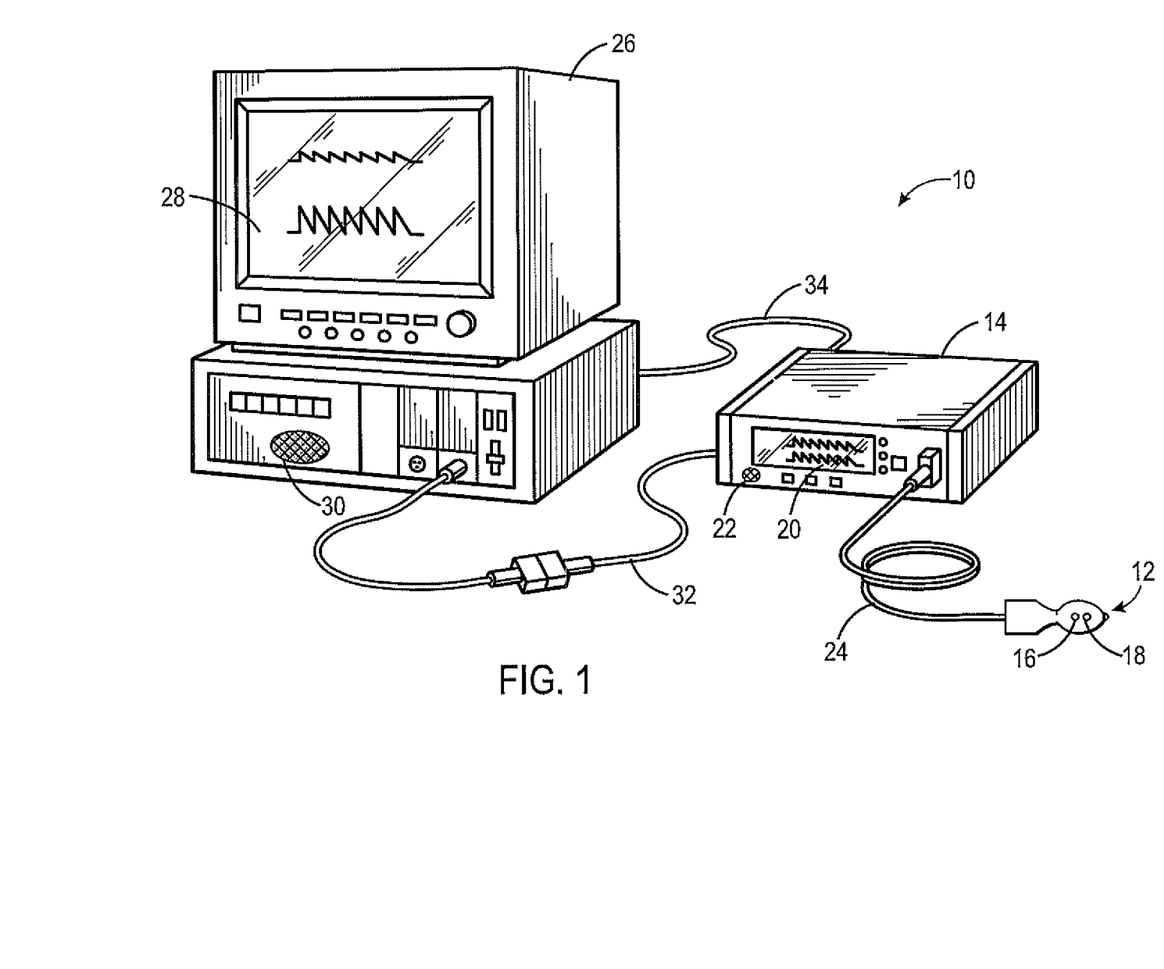
FIG. 1 is a perspective view of a pulse oximeter coupled to a multi-parameter patient monitor and a sensor in accordance with an embodiment.

FIG. 1 is a perspective view of a pulse oximetry system 10 in accordance with embodiments of the present disclosure. The system 10 includes a sensor 12 and a pulse oximetry monitor 14. The sensor 12 includes an emitter 16 for emitting light at certain wavelengths into a patient's tissue and a detector 18 for detecting the light after it is transmitted or scattered through the patient's tissue. The monitor 14 may be capable of calculating physiological characteristics based on the signals received from the sensor 12 relating to light emission and detection. Further, the monitor 14 includes a display 20 capable of displaying the physiological characteristics, historical trends of the physiological characteristics, other information about the system, and/or alarm indications. The monitor 14 may include a speaker 22 to provide an audible alarm in the event that the patient's physiological characteristics cross an alarm threshold. The sensor 12 is communicatively coupled to the monitor 14 via a cable 24. However, in other embodiments a wireless transmission device or the like may be utilized instead of or in addition to the cable 24.

In the illustrated embodiment, the pulse oximetry system 10 also includes a multi-parameter patient monitor 26. In addition to the monitor 14, or alternatively, the multi-parameter patient monitor 26 may be capable of calculating physiological characteristics and providing a central display 28 for information from the monitor 14 and from other medical monitoring devices or systems. For example, the multi-parameter patient monitor 26 may display a patient's $SpO_2$ and pulse rate information from the monitor 14 and blood pressure from a blood pressure monitor on the display 28. Additionally, the multi-parameter patient monitor 26 may indicate an alarm condition via the display 28 and/or a speaker 30 if the patient's physiological characteristics are found to be outside of the normal range. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations.

Figure 2:
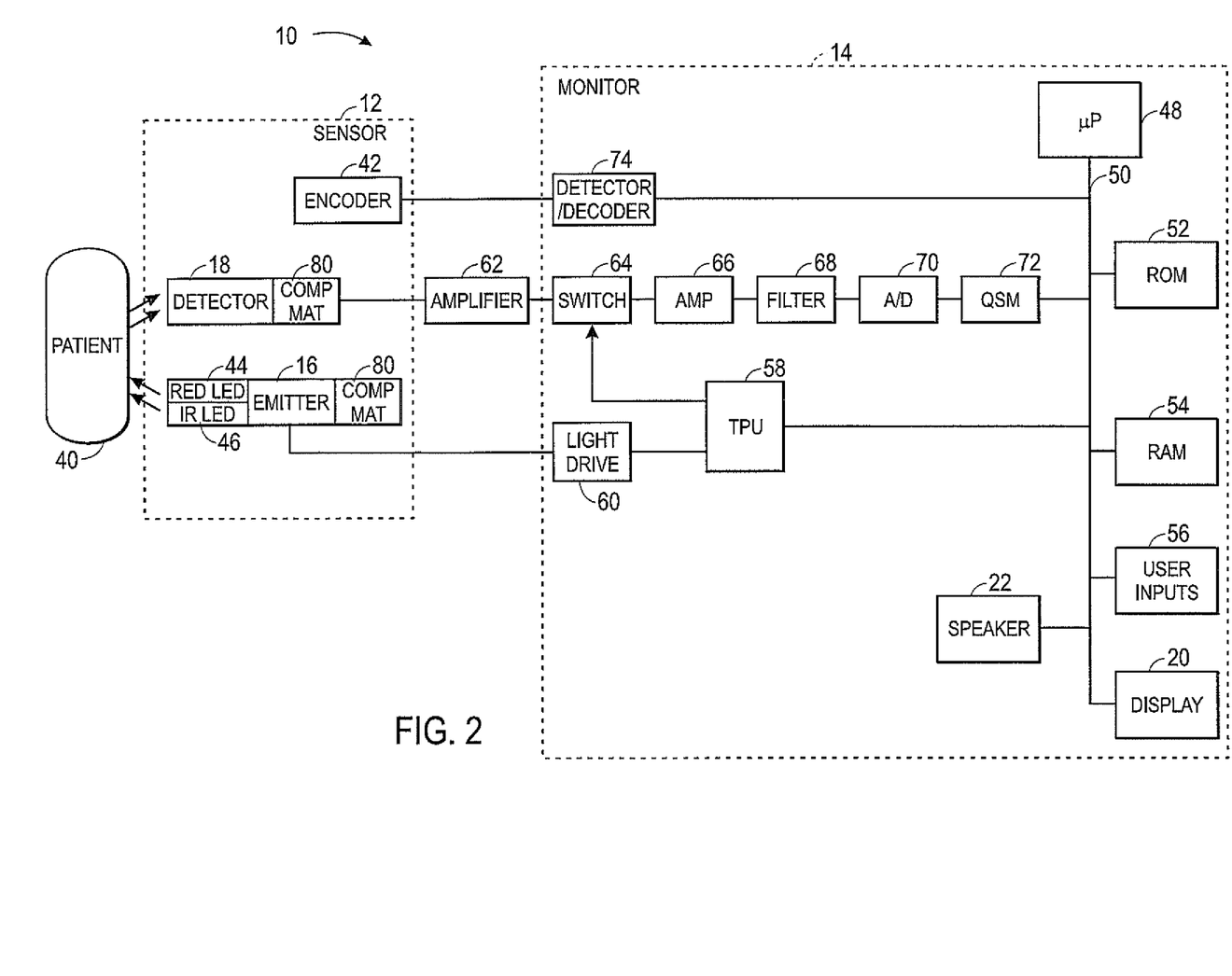
FIG. 2 is a block diagram of the pulse oximeter and sensor coupled to a patient in accordance with an embodiment.

FIG. 2 is a block diagram of the pulse oximetry system 10 of FIG. 1 coupled to a patient 40 in accordance with present embodiments. Specifically, certain components of the sensor 12 and the monitor 14 are illustrated in FIG. 2. The sensor 12 may include the emitter 16, the detector 18, and an encoder 42. It should be noted that the emitter 16 may be capable of emitting one or more wavelengths of light, e.g., RED and IR, into the patient's tissue 40. Hence, the emitter 16 may include a RED LED 44 and an IR LED 46 for emitting light into the patient's tissue 40 at the wavelengths used to calculate the patient's physiological characteristics. In certain embodiments, the RED wavelength may be between about 600 nm and about 700 nm, and the IR wavelength may be between about 800 nm and about 1000 nm. Alternative light sources may be used in other embodiments. For example, a single wide-spectrum light source may be used, and the detector 18 may be capable of detecting certain wavelengths of light. In another example, the detector 18 may detect a wide spectrum of wavelengths of light, and the monitor 14 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 18 may be capable of detecting the intensity of light at the RED and IR wavelengths. In operation, light enters the detector 18 after passing through the patient's tissue 40. The detector 18 may convert the intensity of the received light into an electrical signal. The received light intensity may be directly related to the absorbance and/or scattering of light in the tissue 40. That is, when more light at a certain wavelength is absorbed or scattered, less light of that wavelength is typically received from the tissue by the detector 18. After converting the received light to an electrical signal, the detector 18 may send the signal to the monitor 14, where physiological characteristics may be calculated based at least in part on the relative absorption of the RED and IR wavelengths in the patient's tissue 40.

The encoder 42 may contain information about the sensor 12, such as what type of sensor it is (e.g., whether the sensor is intended for placement on a forehead or digit) as well as characteristics specific to the emitter and/or detector components. 16. This information may allow the monitor 14 to select appropriate algorithms and/or calibration coefficients for calculating the patient's physiological characteristics. The encoder 42 may, for instance, be a coded resistor which stores values corresponding to the type of the sensor 12 and/or the component characteristics. 16. These coded values may be communicated to the monitor 14, which determines how to calculate the patient's physiological characteristics. In another embodiment, the encoder 42 may be a memory on which one or more of the following information may be stored for communication to the monitor 14: the type of the sensor 12; the component characteristics 16; and the proper calibration coefficients and/or algorithms to be used for calculating the patient's physiological characteristics. While the depicted embodiment of FIG. 2 illustrates the encoder 42 as being placed in the sensor 12, in other embodiments the encoder 42 may be placed in a cable (such as cable 24 of FIG. 1) connecting the sensor 12 to the monitor 14.

Signals from the detector 18 and the encoder 42 may be transmitted to the monitor 14. The monitor 14 generally may include processors 48 connected to an internal bus 50. Also connected to the bus may be a read-only memory (ROM) 52, a random access memory (RAM) 54, user inputs 56, the display 20, or the speaker 22. A time processing unit (TPU) 58 may provide timing control signals to a light drive circuitry 60 which controls when the emitter 16 is illuminated and the multiplexed timing for the RED LED 44 and the IR LED 46. The TPU 58 controls the gating-in of signals from detector 18 through an amplifier 62 and a switching circuit 64. These signals may be sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 for later downloading to the RAM 54 as the QSM 72 fills up. In one embodiment, there may be multiple separate parallel paths having the amplifier 66, the filter 68, and the A/D converter 70 for multiple light wavelengths or spectra received.

The processor(s) 48 may determine the patient's physiological characteristics, such as $SpO_2$ and pulse rate, using various algorithms and/or look-up tables based generally on the value of the received signals corresponding to the light received by the detector 18. Signals corresponding to information about the sensor 12 may be transmitted from the encoder 42 to a decoder 74. The decoder 74 may translate these signals to enable the microprocessor to determine the proper method for calculating the patient's physiological characteristics, for example, based generally on algorithms or look-up tables stored in the ROM 52. In addition, or alternatively, the encoder 42 may contain the algorithms or look-up tables for calculating the patient's physiological characteristics.

While the preceding generally describes the electrical and optical operation of a system 10 (such as a pulse oximetry system or other spectrophotometric system), the sensor 12 may include structural features that affect the performance of such a system 10. For example, in an embodiment, the sensor 12 may include collapsible material 80, such as a mesh, a foam having an open-cell structure, a closed-cell structure, or some combination of open and closed cells, a pliable rubber, or a gel-layer, situated opposite the patient tissue 40 relative to the optical components (e.g., the detector 18 and/or the emitter 16). The pressure holding the optical components against the tissue 40 may be regulated by the collapsible material 80 such that this pressure remains within a desired range, ensuring intimate contact between the sensing components and the sensing site while minimizing excessive localized pressure. such as between the diastolic arterial and venous pressure observed for the patient at the site of the sensor 12.

For example, turning to FIGS. 3-6, partial cross-sections of sensors 12 are depicted in accordance with embodiments of the present disclosure. As depicted, the sensor 12 may include an emitter 16, detector 18, and/or cable 24. Conductive elements (e.g., wires) within the cable 24 may be electrically coupled to one or more conductive traces or layers 84 of the sensor 12 that electrically connect the detector 18 and the emitter 16. Patient-contacting surfaces 88 of the sensor 12 may be provided and may be formed from a conformable or shaped material to accommodate the tissue surface when the sensor 12 is placed on a patient and/or to block ambient light from the measurement site. In an embodiment where the sensor 12 is a bandage-style sensor, the patient-contacting surfaces 88 may include an adhesive for securing the sensor 12 to the tissue at the measurement site.

Figure 3:
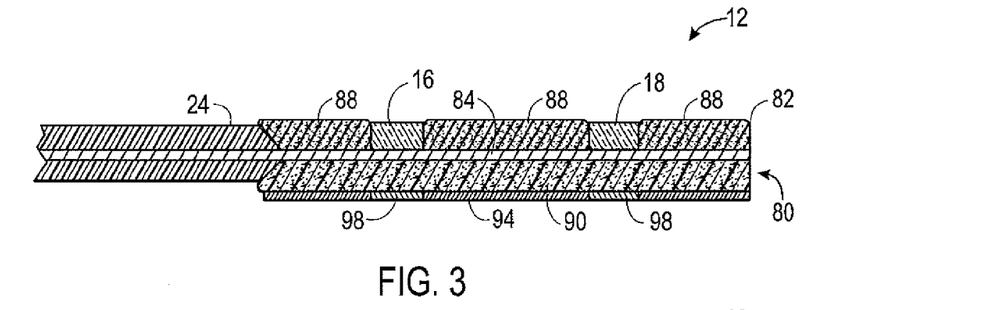
FIG. 3 is a cross-sectional view of a sensor in accordance with an embodiment.

In an embodiment depicted in FIG. 3, a bandage style sensor 82 is provided. That is, the bandage style sensor 82 may be flexible with an adhesive coating to enable adhesion of the sensor 12 to a patient's tissue. In an embodiment, the sensor 12 incorporating a layer of collapsible material 80 in the form of a woven, mesh, or honeycomb type of material may be provided that collapses or remains expanded, depending on the pressure being applied against the material 80. The collapsible material 80 may be provided on the non-patient facing side of the optical components (e.g., emitter 16 and detector 18) and the patient contacting surfaces 88 such that the pressure applied by these structures against the patient surface may be regulated by the degree of expansion or compression of the collapsible material 80.

In an embodiment, the collapsible material 80 may be selected such that the pressure required to compress the material is below the desired maximum pressure threshold (such as that which could result in tissue damage over prolonged use) for the monitoring site. In this embodiment, the collapsible material 80 may remain in an expanded configuration if the applied pressure is less than the pressure threshold, causing the optical components to remain in contact with the monitoring site. However, if the applied pressure exceeds this threshold, the collapsible material 80 may collapse in proportion to the applied pressure, thereby reducing the localized pressure between the component and the monitoring site. In an embodiment, if the applied pressure is less than a minimum threshold pressure (such as that required to ensure intimate contact between sensing components and the monitoring site, and is dependent on the sensor material characteristics and configuration) the collapsible material 80 may remain expanded to maintain the localized contact pressure at the minimum pressure threshold.

Typical venous pressure and diastolic arterial pressures may be less than 10-35 mmHg and 80 mmHg, respectively. Accordingly, in an embodiment, the collapsible material 80 may remain expanded when the applied pressure is insufficient to provide pressure greater than an average venous pressure of 10-35 mmHg and/or may compress or collapse when the applied pressure exceeds an average diastolic arterial pressure of 80 mmHg. In this manner, the collapsible material 80 may modulate the applied pressure to adjust for applied pressures less than the venous pressure and greater than the diastolic arterial pressure.

In an embodiment, the sensor 12 depicted in FIG. 3 may include a backing layer 94 that is relatively rigid in comparison to the collapsible material 80. In an embodiment, the backing layer 94 may be formed from a plastic, composite, or a metal, though in other embodiments, the backing layer 94 may be merely formed from a material that is relatively inelastic or incompressible relative to the collapsible material 80, such as a cloth or tape backing layer.

In an embodiment, windows 98 (such as clear or transparent plastic windows) may be situated in the backing layer 94 over the collapsible material 80, such as over the emitter 16 and/or the detector 18. The windows 98 may allow an operator to determine the state of compression or expansion of the collapsible material 80 in an embodiment where the collapsible material 80 provides a visual indication, such as a calorimetric indication, of the degree of expansion or compression of the collapsible material 80. The collapsible material 80 may also be one color on the interior and another color on the surface, such that, in one embodiment, if the compressible material 80 is compressed beyond a certain degree the interior color shows through or shows to a greater extent. In an embodiment, the collapsible material 80 may be less thick when compressed and may allow an underlying color of another structure of the sensor 12, such as the conductive layer 84 and/or the emitter 16 or detector 18 to be visible through the window 98 when the collapsible material 80 is compressed. In this manner, an operator may, by observing the window 96, determine the degree of compression or expansion of the collapsible material 80 and may thereby adjust the applied pressure at the measurement site.

Figure 4:
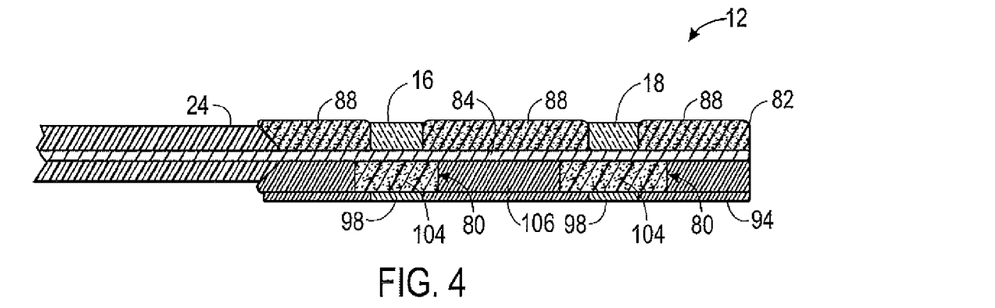
FIG. 4 is a cross-sectional view of a sensor in accordance with an embodiment.

While the preceding describes an embodiment, in which the collapsible material 80 may be provided as a layer 90, FIG. 4 depicts an embodiment in which the collapsible material 80 may be provided as pockets 104 behind the emitter 16 and/or detector 18 separated by spacers 106 made of a different material. The collapse and/or expansion provided by the collapsible material 80 may be localized behind the optical components, though the overall applied pressure applied by the sensor 12 may still be regulated by the collapse and/or expansion of the pockets 104 of collapsible material 80.

Figure 5:
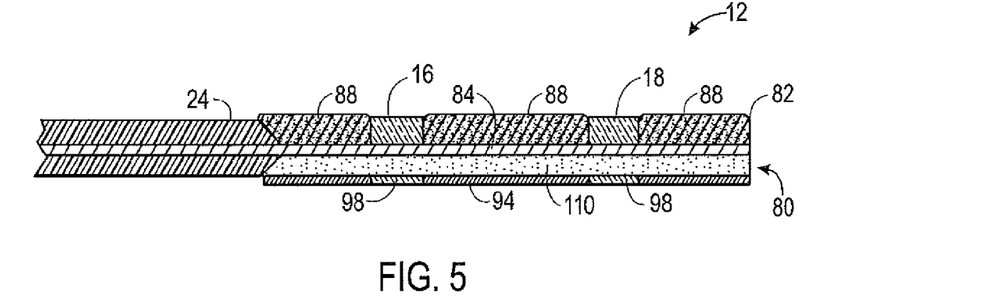
FIG. 5 is a cross-sectional view of a sensor in accordance with an embodiment.

Referring now to FIG. 5, in an embodiment the collapsible material 80 may be provided as a gel layer 110 which thins or expands based on the contact pressure. That is, the gel layer 110 may be thin in response to excessive applied pressures to reduce the effective localized pressure at the measurement site. Conversely, the gel layer 110 may remain at its initial thickness in response to under applied pressures at the measurement site to increase the effective localized pressure at the measurement site.

In an embodiment, the gel layer 110 may be colored such that the thickness of the gel layer 110, and the corresponding pressure applied at the measurement site by the sensor 12, may be determined through the window 98. That is, in an embodiment in which the gel layer 110 is colored, the thickness of the gel layer 110 may be ascertained from the observed color through the window 98. The observed color may decrease or become more transparent as the gel layer 110 thins when under pressure. Conversely, an un-thinned gel layer 110 may more clearly display the color and/or may be more opaque.

Figure 6:
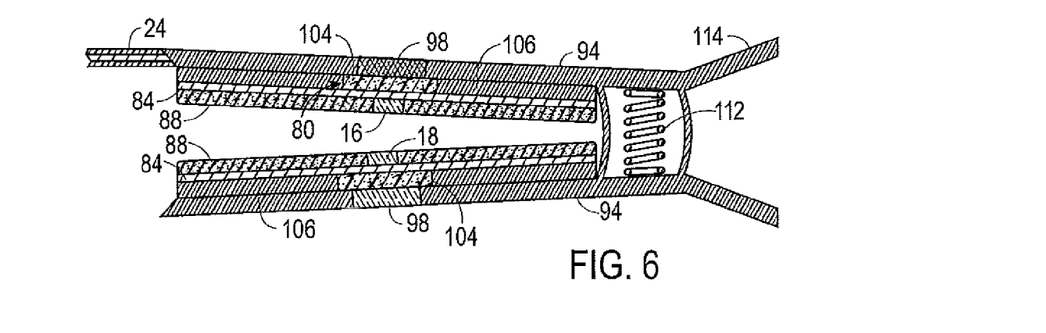
FIG. 6 is a cross-sectional view of a sensor in accordance with an embodiment.

While the preceding figures depict disposable, e.g., bandage-style, sensors, FIG. 6 depicts an embodiment that may be based on a reusable, clip-style sensor 114. The collapsible material 80 may be provided as pockets 104 behind the optical components, e.g., emitter 16 and detector 18. The pressure applied to a measurement site by the biasing effect of a spring 112 or other biasing component of the clip-style sensor 114 may be modulated by the collapse and/or expansion of the collapsible material 80 within the pockets 104 such that the applied pressure ensures sensing component contact while minimizing excessive localized pressure.

The preceding discussion relates various configurations of the sensor 12 that may benefit from the present disclosure. As will be appreciated, the provided examples are not exhaustive and other configurations or combinations of the provided configurations are also possible and fall within the scope of the present disclosure.

Referring now to FIGS. 7-12 an embodiment of the sensor 12 in accordance with the present disclosure is depicted as applied to the tissue 40 of a patient. The sensor 12 may include a layer 90 or pocket 104 of collapsible material 80 in various states of expansion and/or collapse. In addition, the sensor 12 may include an emitter 16 or detector 18 and patient-contacting surfaces 88 that interface with the tissue 40 of the patient. The sensor 12 may also include a backing layer 94, such as a rigid or semi-rigid layer of material, and a window 98 through which an operator may observe the state of compression of the collapsible material 80.

Figure 7:
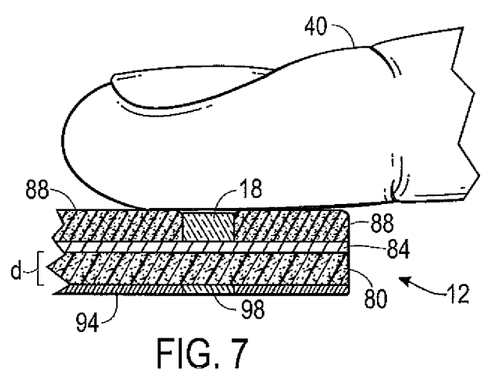
FIG. 7 is a cross-sectional view of a sensor applied to tissue in accordance with an embodiment.
Figure 8:
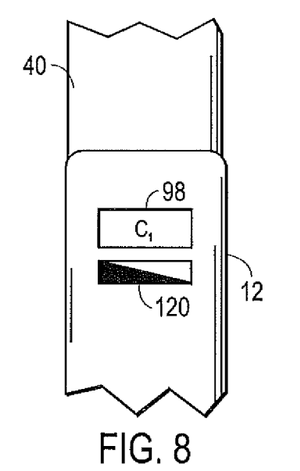
FIG. 8 is an overhead view of the sensor of FIG. 7 in accordance with an embodiment.

In FIGS. 7 and 8 the sensor 12 is depicted as being placed on tissue 40, such as a finger, with a relatively loose applied pressure. In this scenario, the collapsible material 80 may remain in an expanded state to press the detector 18 and/or other patient-contacting components against the tissue 40 with enough pressure to ensure proper contact with the tissue 40. As depicted in the cross-sectional view of FIG. 7, in this state the layer 90 or pocket 104 of collapsible material 80 may be in an expanded state of thickness d. In an embodiment in which the thickness of the layer 90 or pocket 104 of collapsible material 80 provides a colorimetric indication of expansion or compression, the window 98 may be used to view a color, $c_1$, indicative of the expanded state of the collapsible material 80, as depicted in the overhead view of FIG. 8.

In an embodiment, a color scale or chart 120 may be provided for an operator to compare the color visible in the window 98, such as the color $c_1$, to the scale, allowing the operator to determine the localized contact pressure applied by the sensor 12, i.e., is the sensor loose, tight, or within acceptable parameters. If the applied pressure is not within acceptable parameters, the operator may choose to reapply the sensor 12 to the tissue 40, such as to loosen or tighten the sensor 12. In an embodiment, a color scale 120 may be provided on the sensor 12 itself, such as proximate or adjacent to the window 98 for convenient reference.

Figure 9:
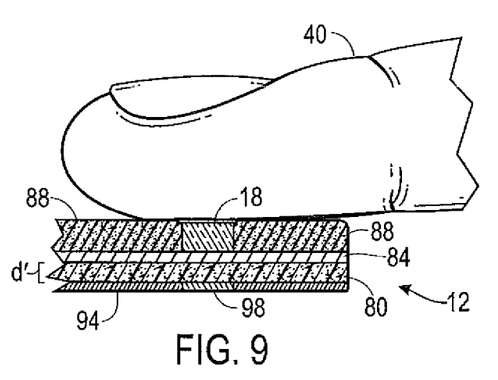
FIG. 9 is a cross-sectional view of a sensor applied to tissue in accordance with an embodiment.
Figure 10:
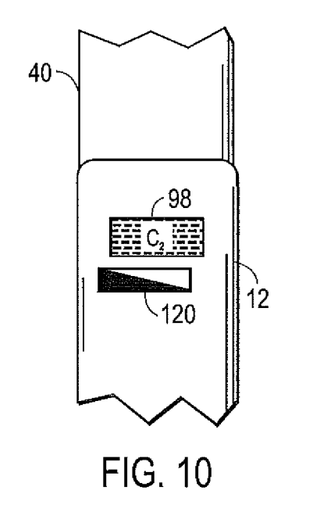
FIG. 10 is an overhead view of the sensor of FIG. 9 in accordance with an embodiment.

In FIGS. 9 and 10 the sensor 12 is depicted as being placed on tissue 40, such as a finger, with an intermediate pressure, such as a pressure suitably within the bounds of the venous pressure and the diastolic arterial pressure of the tissue 40. In this scenario, the collapsible material 80 may be in an intermediate state where some compression has occurred, i.e., the collapsible material 80 is not fully expanded, and the contact pressure is regulated to maintain the detector 18 and/or other patient-contacting components against the tissue 40 at a pressure between the venous pressure and the diastolic arterial pressure associated with the tissue 40. As depicted in the cross-sectional view of FIG. 9, in this state the layer 90 or pocket 104 of collapsible material 80 may be in an intermediate state of thickness d'. In an embodiment in which the thickness of the layer 90 or pocket 104 of collapsible material 80 provides a colorimetric indication of expansion or compression, the window 98 may be used to view a color, $c_2$, indicative of the intermediate state of the collapsible material 80, as depicted in the overhead view of FIG. 10.

Figure 11:
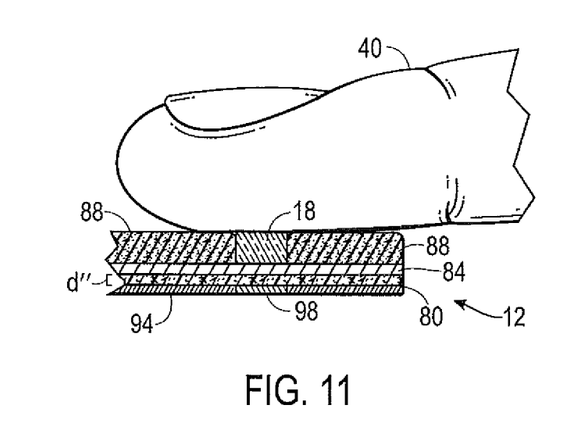
FIG. 11 is a cross-sectional view of a sensor applied to tissue in accordance with an embodiment.
Figure 12:
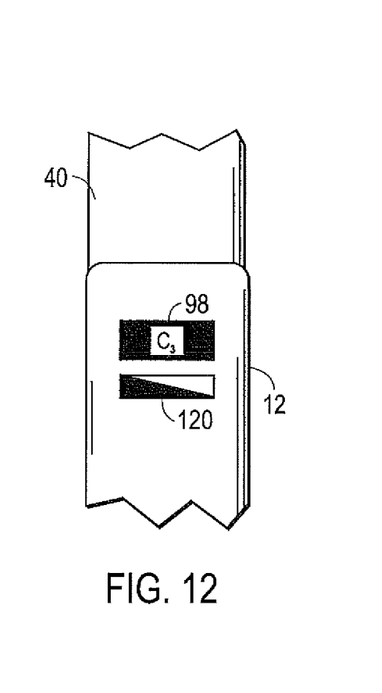
FIG. 12 is an overhead view of the sensor of FIG. 11 in accordance with an embodiment.

In FIGS. 11 and 12 the sensor 12 is depicted as being placed on tissue 40, such as a finger, with a relatively tight applied pressure. In this scenario, the collapsible material 80 may be in a collapsed state to reduce the pressure of the detector 18 and/or other patient-contacting components against the tissue 40. As depicted in the cross-sectional view of FIG. 11, in this state the layer 90 or pocket 104 of collapsible material 80 may be in a collapsed state of thickness d''. In an embodiment in which the thickness of the layer 90 or pocket 104 of collapsible material 80 provides a calorimetric indication of expansion or compression, the window 98 may be used to view a color, $c_3$, indicative of the collapsed state of the collapsible material 80, as depicted in the overhead view of FIG. 12.

While the preceding discussion of FIGS. 7-12 provides examples of discrete calorimetric indicators, i.e., $c_1$, $c_2$, $c_3$, configurations of the sensor 12 are not limited to such discrete implementations. In particular, the calorimetric indication may span a continuum or spectrum of possible color or grayscale indications as opposed to being a discrete color indication. Likewise, the color scale 120 may accommodate such a continuous or spectral display of color by depicting a continuum with markers or indications on the displayed continuum as to different pressure levels of interest.

The preceding discussion has been provided in the context of a pulse oximetry system 10 and sensor 12 to facilitate explanation of the concepts of the present disclosure; however, the preceding discussion should not be understood as limiting the present disclosure to such pulse oximetry applications. Instead, the present sensor configurations may be employed with other types of spectrophotometric systems and sensors or with other systems where a sensor is applied to a tissue (or other surface) within certain contact pressure requirements.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. The invention is to cover all modifications, equivalents, and alternatives falling within the spirit and scope of the invention as defined by the following appended claims.

What is claimed is:

1. A sensor, comprising:
a light emitting component comprising a first patient-contacting surface and a first opposing surface;
a light detecting component comprising a second patient-contacting surface and a second opposing surface and configured to detect light energy emitted by the light emitting component incident upon the second patient-contacting surface;
a backing layer; and
a collapsible material positioned between the backing layer and at least one of the first opposing surface or the second opposing surface, wherein the collapsible material, when applied to a tissue, is configured to maintain an expanded configuration under a first pressure below a first threshold, is configured to maintain a partially collapsed configuration under a second pressure above the first threshold and below a second threshold, and is configured to maintain a collapsed configuration under a third pressure above the first threshold and the second threshold, wherein the first threshold is in a range of 10 mmHg to 35 mmHg, and wherein the second threshold is at least 80 mmHg.

2. The sensor of claim 1, wherein the collapsible material comprises a woven material.

3. The sensor of claim 1, wherein the collapsible material comprises a foam material comprising open cells, closed cells, and/or a combination thereof.

4. The sensor of claim 1, wherein the collapsible material comprises a gel.

5. The sensor of claim 1, wherein the collapsible material is a different color based on the degree of expansion or compression of the collapsible material.

6. The sensor of claim 1, comprising a window situated above the collapsible material such that a color of the collapsible material may be viewed.

7. The sensor of claim 1, wherein the backing layer comprises a window situated above the collapsible material through which the thickness of the collapsible material may be visually determined.

8. The sensor of claim 1, wherein the first threshold comprises a pressure which maintains intimate contact between the sensing component and the monitoring site and the second threshold comprises a pressure level which minimizes excessive localized pressure which could result in tissue damage over prolonged periods of use.

9. The sensor of claim 1, wherein the collapsible material comprises a mesh material.

10. The sensor of claim 1, wherein the collapsible material comprises a material having honeycombed cells.

11. The sensor of claim 1, wherein a tissue pressure exerted on a patient tissue by one or more of the first patient-contacting surface or the second patient-contacting surface is 10-35 mmHg in the expanded configuration.

12. A system, comprising:
a monitor; and
a sensor in electrical communication with the monitor, the sensor comprising:
an emitter;
a detector configured to generate an electrical signal in response to light emitted by the emitter;
a backing layer; and
a collapsible material situated between the backing layer and at least one of the emitter or the detector, wherein the collapsible material is configured to maintain a pressure between a venous pressure and an arterial pressure when the sensor is applied; and
wherein the sensor comprises a window within the backing layer through which a colorimetric indication of the state of the collapsible material may be determined.

13. A sensor, comprising:
a light emitting component comprising a first patient-contacting surface and a first opposing surface;
a light detecting component comprising a second patient-contacting surface and a second opposing surface and configured to detect light energy emitted by the light emitting component incident upon the second patient-contacting surface;
a backing layer; and
a collapsible material positioned between the backing layer and at least one of the first opposing surface or the second opposing surface, wherein the collapsible material, when applied to a tissue, is configured to maintain an expanded configuration under a first pressure below a first threshold, is configured to maintain a partially collapsed configuration under a second pressure above the first threshold and below a second threshold, and is configured to maintain a collapsed configuration under a third pressure above the first threshold and the second threshold, and wherein the collapsible material comprises a woven material.

14. A sensor, comprising:
a light emitting component comprising a first patient-contacting surface and a first opposing surface;
a light detecting component comprising a second patient-contacting surface and a second opposing surface and configured to detect light energy emitted by the light emitting component incident upon the second patient-contacting surface;
a backing layer; and
a collapsible material positioned between the backing layer and at least one of the first opposing surface or the second opposing surface, wherein the collapsible material, when applied to a tissue, is configured to maintain an expanded configuration under a first pressure below a first threshold, is configured to maintain a partially collapsed configuration under a second pressure above the first threshold and below a second threshold, and is configured to maintain a collapsed configuration under a third pressure above the first threshold and the second threshold, and wherein the collapsible material comprises a mesh material.

15. A sensor, comprising:
a light emitting component comprising a first patient-contacting surface and a first opposing surface;
a light detecting component comprising a second patient-contacting surface and a second opposing surface and configured to detect light energy emitted by the light emitting component incident upon the second patient-contacting surface;
a backing layer; and
a collapsible material positioned between the backing layer and at least one of the first opposing surface or the second opposing surface, wherein the collapsible material, when applied to a tissue, is configured to maintain an expanded configuration under a first pressure below a first threshold, is configured to maintain a partially collapsed configuration under a second pressure above the first threshold and below a second threshold, and is configured to maintain a collapsed configuration under a third pressure above the first threshold and the second threshold, and wherein the collapsible material comprises a material having honeycombed cells.

16. A sensor, comprising:
a light emitting component comprising a first patient-contacting surface and a first opposing surface;
a light detecting component comprising a second patient-contacting surface and a second opposing surface and configured to detect light energy emitted by the light emitting component incident upon the second patient-contacting surface;
a backing layer; and
a collapsible material positioned between the backing layer and at least one of the first opposing surface or the second opposing surface, wherein the collapsible material, when applied to a tissue, is configured to maintain an expanded configuration under a first pressure below a first threshold, is configured to maintain a partially collapsed configuration under a second pressure above the first threshold and below a second threshold, and is configured to maintain a collapsed configuration under a third pressure above the first threshold and the second threshold; and
wherein the backing layer comprises a window situated above the collapsible material through which the thickness of the collapsible material may be visually determined.

* * * * *